(12) United States Patent
Tao et al.

(10) Patent No.: US 11,480,573 B2
(45) Date of Patent: Oct. 25, 2022

(54) PHOSPHOPROTEINS IN EXTRACELLULAR VESICLES AS CANDIDATE MARKERS FOR BREAST CANCER

(71) Applicant: Purdue Research Foundation, West Lafayette, IN (US)

(72) Inventors: Weiguo Andy Tao, West Lafayette, IN (US); Anton B. Ilyuk, West Lafayette, IN (US); Hillary Andaluz, Lafayette, IN (US); I-Hsuan Chen, West Lafayette, IN (US); Li Pan, Lawrenceville, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 98 days.

(21) Appl. No.: 15/864,376

(22) Filed: Jan. 8, 2018

(65) Prior Publication Data
US 2018/0196051 A1    Jul. 12, 2018

Related U.S. Application Data

(60) Provisional application No. 62/443,400, filed on Jan. 6, 2017.

(51) Int. Cl.
*G01N 33/50* (2006.01)
*G01N 33/574* (2006.01)
*G01N 33/68* (2006.01)

(52) U.S. Cl.
CPC . *G01N 33/57415* (2013.01); *G01N 33/57488* (2013.01); *G01N 33/6842* (2013.01); *G01N 33/6848* (2013.01)

(58) Field of Classification Search
CPC ............................................. G01N 33/57415
USPC ....................................................... 435/7.23
See application file for complete search history.

(56) References Cited

PUBLICATIONS

Xie et al (Electrophoresis, 2010, 3(11): 1842-1852).*
Monterminl et al (JBC, 2015, 290(04): 24534-24546).*
Hill et al (Proteome Science, 2009, 7(2): 1-17).*
Khan et al (PLOS One, 2012, 7(10): 1-10).*
Logozzi et al (PLOS One, 2009, 4(4): 1-10).*
Muller et al (J Immunol Methods, 2014, 411: 55-65).*
Tockman et al (Cancer Res., 1992, 52:2711s-2718s).*
Schey et al (Methods, 2015, 87: 75-82).*
Adamczyk et al (Life Sciences, 2011, 89: 304-312).*
Carayon et al (JBC, 2011, 286(39): 34426-34439).*
Yang et al (Journal of Proteome Research, 2007, 6: 4489-4497).*
"OVA1," The National Cancer Institute Early Detection Research Network, available at https://edrn.nci.nih.gov/data-and-resources/biomarkers/ova1 (last visited Apr. 19, 2021), US.

* cited by examiner

*Primary Examiner* — Sean E Aeder
(74) *Attorney, Agent, or Firm* — Reichel Stohry Dean LLP; Natalie J. Dean; Mark C. Reichel

(57) ABSTRACT

The state of protein phosphorylation and glycosylation can be key determinants of cellular physiology such as early stage cancer, but the development of phosphoproteins and/or glycoproteins in biofluids for disease diagnosis remains elusive. Here we demonstrate, for the first time, a strategy to isolate and identify phosphoproteins/glycoproteins in extracellular vesicles (EVs) from human plasma as potential markers to differentiate disease from healthy states. We identified close to 10,000 unique phosphopeptides in EVs by isolating from small volume of plasma samples. Using label-free quantitative phosphoproteomics, we identified 144 phosphoproteins in plasma EVs that are significantly higher in patients diagnosed with breast cancer than in healthy controls. Several novel biomarkers were validated in individual patients using Paralleled Reaction Monitoring for targeted quantitation. Similarly a group of glycoproteins in plasma EVs are identified. The study demonstrated that the development of phosphoproteins and/or glycoproteins in plasma EV as disease biomarkers is highly feasible and may transform cancer screening and monitoring.

13 Claims, 7 Drawing Sheets

(A) Microvesicles

Exosome (B)

(A)

Microvesicles

Exosome (B)

Microvesicles

Exosome

PHOSPHOPROTEINS IN EXTRACELLULAR VESICLES AS CANDIDATE MARKERS FOR BREAST CANCER

CROSS-REFERENCE

This Application claims the benefit of U.S. Provisional Application 62/443,400, filed on Jan. 6, 2017. The disclosure of which is expressly incorporated herein entirely.

STATEMENT OF GOVERNMENT SUPPORT

This invention was made with government support under GM109626 and GM111788 awarded by the National Institutes of Health, and CHE1506752 awarded by the National Science Foundation. The government has certain rights in the invention.

FIELD OF INVENTION

This disclosure is related to a method to use small portions of patient body fluid sample to diagnose and monitor a pathological disease. Specifically the method uses non-invasive phosphoproteosome technology to identify a panel of phosphoproteins in extracellular vesicles as the biomarkers to diagnose and monitor breast cancer patient in a heterogeneous patient cohorts.

BACKGROUND

Extracellular vesicles (EVs) are produced by all domains of life including complex eukaryotes, both Gram-negative and Gram-positive bacteria, mycobacteria and fungi.

There are many types of EVs. Exosomes are membranous vesicles of endocytic origin (50-100 nm diameter) enriched in CD63 and CD81. Microvesicle (also referred to as shedding microvesicles, SMVs), are shed directly from the plasma membrane, (20-1000 nm). Membrane particles (50-80 nm), or large membranous vesicles (~600 nm) include $CD133^+$ and $CD63^+$. Apoptotic blebs or vesicles (1000-5000 nm diameter) are released by dying cells.

These EVs are often separated by density by differential centrifugation.

In humans, endogenous extracellular vesicles likely play a role in coagulation, intercellular signaling and waste management.

A phosphoprotein a protein that is post-translationally modified by the attachment of either a single phosphate group, or a complex molecule such as 5'-phspho-DNA, through a phosphate group. The target amino acid is usually serine, threonine or tyrosine residues (mostly in eukaryotes), or aspartic acid or histidine residues (mostly in prokaryotes).

Abnormal protein phosphorylation has been implicated in a number of diseases, such as Alzheimer's disease, Parkinson's disease, and other degenerative disorders.

Tau protein belongs to a group of Microtubule Associated Proteins (MAPs) which, among several things, help stabilize microtubules in cells, including neurons. Association and stabilizing activity of tau protein depends on its phosphorylated state. In Alzheimer's disease, due to misfoldings and abnormal conformational changes in tau protein structure, it is rendered ineffective at binding to microtubules and thus unable to keep the neural cytoskeletal structure organized during neural processes; in fact abnormal tau inhibits and disrupts microtubule organization and disengages normal tau from microtubules into cytosolic phase. The misfoldings lead to the abnormal aggregation into fibrillary tangles inside the neurons, the hallmark of Alzheimer's disease. There is an adequate amount that the tau protein needs to be phosphorylated to function, but hyperphosphorylation of tau protein is thought to be one of the major influences on its incapacity to associate. Kinases PP1, PP2A, PP2B, and PP2C dephosphorylate tau protein in vitro, and their activities have found to be reduced in areas of the brain in Alzheimer patients. Tau phosophoprotein is three to fourfold hyperphosphorylated in an Alzheimer patient compared to an aged non-afflicted individual. Alzheimer disease tau seems to remove MAP1 and MAP2 (two other major associated proteins) from microtubules and this deleterious effect is reversed when dephosphorylation is performed, evidencing hyperphosphorylation as the sole cause of the crippling activity.

Parkinson's Disease

α-Synuclein is a protein that is associated with Parkinson's disease. This protein is coded by the PARRK1 gene and in its native form, α-Synuclein is involved in the recycling of the synaptic vesicles that carry neurotransmitters and naturally occurs in an unfolded form. Elevated levels of α-Synuclein are found in patients with Parkinson's disease, and there seems to be a positive correlation between the amount of the α-Synuclein protein present in the patient and the severity of the disease.

Phosphorylation of the amino acid $Ser^{129}$ in the α-Synuclein protein has a profound effect on the severity of the disease. There seem to be correlation between the total α-Synuclein concentration (unphosphorylated) and the severity of the symptoms in Parkinson's disease patients. Healthy patients seem to have higher levels of unphosphorylated α-Synuclein than patients with Parkinson's disease. Moreover, the measurement of the changes in the ratio of concentrations of phosphorylated α-Synuclein to unphosphorylated α-Synuclein within a patient could be a potential marker of the disease progression Phosphorylation of $Ser^{129}$ is associated with the aggregation of the protein and further damage to the nervous system. Furthermore, the aggregation of phosphorylated α-Synuclein can be enhanced if a presynaptic scaffold protein Sept4 is present in insufficient quantities. It is important to note that direct interaction of α-Synuclein with Sept4 protein inhibits the phosphorylation of $Ser^{129}$.

Another post translational signatures found in EV proteins are glycosylation. There are reports glycosignatures of EVs were specific and altered glycosylation within the cell affected the composition and/or dynamics to EVs release. Some identified glycosignatures of EVs may provide novel biomarkers for ovarian cancer. (See Extracelluar Vesicles from Ovarian Carcinoma Cells Display Specific Glycosignatures, Biomolecules 2015 September; 5(3): 1741-1761).

Despite the available knowledge to limited phosphoproteins and/or glycosignatures and diseases, to date, there is no systematic method to decipher the correlation between the phosphoproteins/glycoproteins and various cancer diseases. This disclosure contemplates to meet such needs.

SUMMARY OF THE INVENTION

This disclosure provides a method of diagnosing and monitoring a pathological disease in a heterogeneous patient cohorts using phosphoproteins as the biomarkers. The method comprises the following steps:
(i) Isolating extracellular vesicles (EVs) in an aliquot of plasma from at least one patient blood and from at least one healthy individual blood;
(ii) Enriching phosphoproteins in said isolated EVs;

(iii) Using label-free quantitative phosphoproteomics to identify at least one phosphoprotein from the patient plasma that plasma that the phosphor-level is significantly different from the same phosphoprotein from the healthy control plasma;
(iv) Validating said at least one phosphoprotein in the rest of patient cohorts with parallel reaction monitoring (PRM) or multi-reaction monitoring (MRM) to compile a panel of phosphoproteins; and
(v) Using the panel of phosphoproteins as biomarkers for diagnosing and monitoring said pathological disease.

In one embodiment, the aforementioned method can monitor a pathological disease of breast cancer and the panel of phosphoproteins to serve as the biomarker are listed in Table 1.

In one embodiment, the aforementioned method can monitor breast cancer with phosphoproteins comprising at least Ral GTPase-activating protein subunit alpha-2 (RALGAPA2), cGMP-dependent protein kinase1 (PKG1) and tight junction protein 2 (TJP2).

This disclosure further provides a kit for diagnosing a pathological disease from the biofluid of a patient. The kit may contain antibodies to detect the panel of phosphoproteins identified according to aforementioned method. The antibodies in the kit may detect Ral GTPase-activating protein subunit alpha-2 (RALGAPA2), cGMP-dependent protein kinase1 (PKG1) and tight junction protein 2 (TJP2) for breast cancer patient.

This disclosure further provides a method of diagnosing and monitoring a pathological disease in a heterogeneous patient cohorts using glycoproteins as biomarkers. The method comprises the following steps:
(i) Isolating extracellular vesicles (EVs) in an aliquot of plasma from at least one patient blood and from at least one healthy individual blood;
(ii) Enriching glycoproteins in said isolated EVs;
(iii) Using label-free quantitative glycoproteomics to identify at least one glycoprotein from the patient plasma that plasma that the glycosylation level is significantly different from the same glycoprotein from the healthy control plasma;
(iv) Validating said at least one glycoprotein in the rest of patient cohorts with parallel reaction monitoring (PRM) or multi-reaction monitoring (MRM) to compile a panel of glycoproteins; and
(v) Using the panel of glycoproteins as biomarkers for diagnosing and monitoring said pathological disease.

In one embodiment, the aforementioned method can monitor a pathological disease of breast cancer and the panel of glycoproteins to serve as the biomarker are listed in Table 2.

In yet another embodiment, the method of monitoring a pathological disease of breast cancer comprising to identifying and validating the presence of signature proteins found in Table 1, Table 2 or the combination thereof.

These and other features, aspects and advantages of the present invention will become better understood with reference to the following figures, associated descriptions and claims.

DETAILED DESCRIPTION

Figure 1:
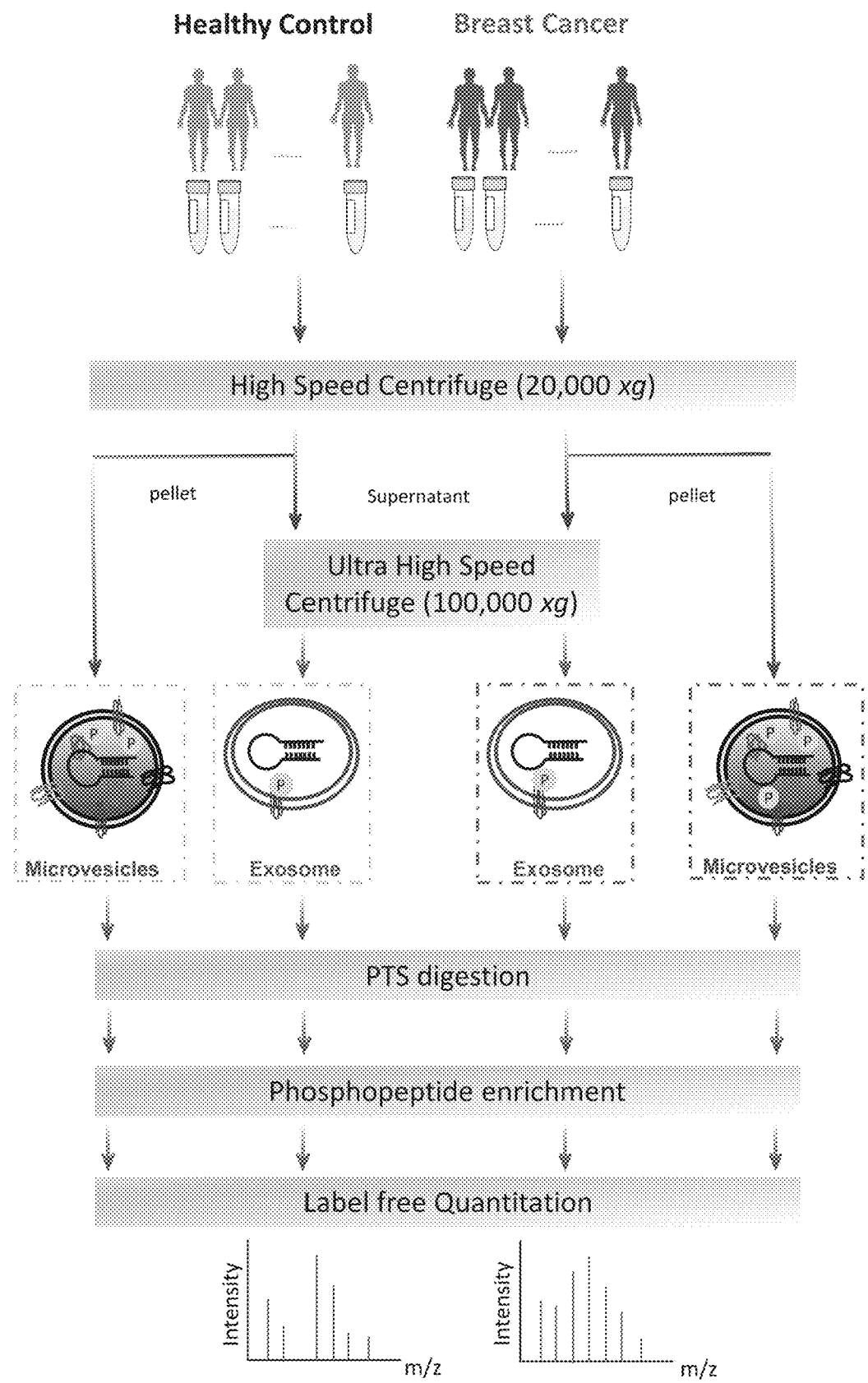
FIG. 1 The workflow for revealing breast cancer extracellular vesicles phosphoproteomic. A total of 18 breast cancer patients and 6 healthy controls were used in this study. After sequential high speed centrifuge to isolate extracellular vesicles, PTS digestion was performed, and the resulting phosphopeptides were enriched by IMAC tip.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Early diagnosing and monitoring diseases such as cancer through blood tests has been a decade-long aim of medical diagnostics. Since protein phosphorylation is one of the most important and widespread molecular regulatory mechanisms that controls almost all aspects of cellular functions, the status of a phosphorylation event conceivably provides clues regarding disease states. However, few phosphoproteins have been developed as disease markers. Phosphoprotein assay from tissues face tremendous challenges due to invasive nature of tissue biopsy and highly dynamics of protein phosphorylation during the typically long and complex procedure. Furthermore, biopsy tissue from tumors is simply not available for monitoring patient response over the course of treatment. Development of phosphoproteins as disease biomarkers from biofluids is even more challenging due to the presence of active phosphatases in high concentration in blood. With a few high abundant proteins representing over 95% of the mass in blood, few phosphorylated proteins in plasma/serum could be identified with stable and detectable concentration.

Recent discovery of extracellular vesicles (EVs), including microvesicles and exosomes, and their potentially important cellular functions has presented them as intriguing sources for biomarker discovery and disease diagnosis. Critical for immune regulation and intercellular communication, EVs have many differentiating characteristics of cancer cell-derived cargo, including mutations, active miRNA, and signaling molecules with metastatic features. The growing body of functional studies have provided strong evidence that these EV-based disease markers can be identified well before the onset of symptoms or physiological detection of a tumor, making them a promising candidate for early-stage cancer and other disease detection. Interestingly, EVs are membrane-encapsulated nano- or microparticles, which protects their inside contents from external proteases and other enzymes. These features make them highly stable in a biofluid for extended periods of time, and also allow us to potentially develop phosphoproteins in EVs for medical diagnoses. The ability to detect the genome output—active proteins, in particular phosphoproteins—can arguably provide more direct real-time information about the organism's physiological functions and disease progression, particularly in cancer.

We aimed to develop EV phosphoproteins as potential disease markers by focusing on the breast cancer in this study. To this end, we isolated and identified the largest group of EV phosphoproteins from both microvesicles and exosomes to date, and measured phosphorylation changes across breast cancer patients and healthy individuals. We subsequently identified multiple potential candidates and verified several among 18 patients and 6 healthy controls. The study demonstrated here can be applied to other systems and thus establish a new strategy for biomarker discovery.

MS-based proteomic profiling and quantitation holds enormous promise for uncovering new biomarkers. However, successful applications to human disease remain limited. This is, in large part, due to the complicity of biofluids that have extremely wide dynamic range and are typically dominated by a few highly abundant proteins, which prevents the development of a coherent, practical pipeline for systemic screening and validation. Here, we report in-depth analyses of phosphoproteomes in plasma EVs and demonstrate the feasibility of developing phosphoproteins as potential disease biomarkers. Previous studies typically could only identify a small number of phosphoproteins in plasma, likely due to the presence of phosphatase in the blood stream, and the level of phosphorylation does not have any clear meaningful connection to biological status. We presented an MS-based strategy that includes the isolation of EV particles from human blood, enrichment of EV phosphopeptides, LC-MS/MS analyses, and PRM quantification for biomarker discovery and quantitative verification, in the context of breast cancer to identify novel breast cancer biomarkers meriting further evaluation in larger, heterogeneous patient cohorts. The study highlights an essential feature of this strategy that the ability to isolate and identify thousands of phosphopeptides from limited volumes of human plasma in biobank provides unlimited possibility to explore existing resources for a wide range of diseases.

Similarly, glycoprotein signature in EVs can be identified and validated as those phosphoprotein signatures in EVs.

Recently, liquid biopsies, analysis of biofluids such as plasma and urine, have gained much attention for cancer research and clinical care, since they offer multiple advantages in clinical settings, including non-invasive nature, a suitable sample source for longitudinal disease monitoring, better screenshot of tumor heterogeneity, and so on. Current liquid biopsies primarily focus on the detection and downstream analysis of CTCs (circulating tumor cells) and ctDNA (circulating tumor DNA). The major obstacle with the current methods is the heterogeneity and extreme rarity of the circulating tumor cells and circulating DNA. EVs offer all the same attractive advantages of a liquid biopsy but without the sampling limitation of CTCs and ctDNA. At present, most of studies on EVs focus on microRNAs and a small portion on EV proteins. The ability to detect the genome output, in particular functional proteins such as phosphoproteins, can arguably provide more useful real-time information about the organism's physiological functions and disease progression, such as in cancer early detection and monitoring.

Our study clearly indicated that EV phosphoproteomes can be readily captured and analyzed, and it is interesting to know that EV phosphoproteins are stable over a long period of storage time (the plasma samples from Indiana Biobank were collected over 5 years ago), which is critical for applications in clinical tests. However, a thorough investigation on EV phophoproteome stability might be necessary, since cellular phosphorylation events are extremely dynamic and EVs are circulating in the blood for long period of time. EV phosphoproteomes may mainly represent phosphorylation events that are constitutively active and therefore insensitive to capture acute events. All these questions can be addressed with further studies on well-defined EV samples, preferably using animal models.

We present here a feasible strategy to develop phosphoproteins as potential disease markers. The strategy relies on the isolation of a good quantity of EVs with high reproducibility. At this stage, the isolation of microvesicles and exosomes is primarily based on differential high speed centrifugation, which may need further improvement for clinical settings. Bias and contaminations introduced by immunoprecipitation of microvesicles and exosomes from plasma proteins need to be avoided. The development of phosphoproteins as biomarkers also demand the availability of phospho-specific antibodies. Alternatively, in addition to develop ELISA or similar immuno-based assays, other validation methods such as MS-base targeted quantitation and non-antibody based methods are contemplated for validating the phosphoprotein based diagnosis. Taken into the consideration of the complexity of biofluids and the necessity to include EV isolation and phosphopeptide isolation in sample preparation, further developing of the accuracy of MS-based targeted quantitation of heterogeneous clinical samples is necessary.

The strategy used for developing phosphoproteins as potential disease markers can be similarly used in developing glycoproteins as disease markers. A preliminary list of glycoproteins listed in Table 2 can be used alone or in combination with the preliminary list of phosphoproteins listed in Table 1 to screen, validate and monitor an exemplary pathological disease, in this case, breast cancer. Other pathological diseases associated with various EV biomarkers can be validated in similar fashion.

MATERIALS AND METHODS

Plasma Samples

The Indiana University Institutional Review Board approved the use of human plasma samples. Blood samples were collected from 6 healthy females and from 30 breast cancer patients that were obtained through the IU Simon Cancer Center/Indiana Biobank. Plasma samples were collected by the standard protocol. In brief, plasma sample processing was initiated within 30 min of blood draw to to an evacuated blood collection tube with EDTA. Samples were spun for 30 min at 3,500 rpm to remove all cell debris and platelet, and stored in −78° C.

Extracellular Vesicle Isolation

A total 5.5 ml pooled plasma samples were collected from both healthy control and breast cancer patient groups for technical replicates on EV phosphoproteomics. Plasma samples were centrifuged at 20,000×g at 4° C. for 1 hr. Pellets were washed with cold PBS and centrifuged again at 20,000×g at 4° C. for 1 hr, the pellets were collected as microvesicles. Supernatants after the first centrifugation were further centrifuged at ultra-high speed 100,000×g at 4° C. for 1 hr. Pellets were wash with cold PBS and centrifuged at 100,000×g for 1 hr again. The pellets collected from the ultra-high speed centrifugation were exosome particles.

Protein Digestion

The digestion was performed with a phase transfer surfactant aids (PTS) procedure EVs were solubilized in lysis buffer containing 12 mM sodium deoxycholate (SDC), 12 mM sodium lauroyl sarcosinate (SLS) and phosphatase inhibitor cocktail (Sigma-Aldrich, St. Louis, Mo.) in 100 mM Tris-HCl, pH8.5. Proteins were reduced and alkylated with 10 mM tris-(2-carboxyethyl)phosphine (TECP) and 40 mM chloroacetamide (CAA) at 95° C. for 5 min. Alkylated proteins were diluted to 5 fold with 50 mM triethylammonium bicarbonate (TEAB) and digested with Lys-C (Wako, Japan) in a 1:100 (w/w) enzyme-to-protein ratio for 3 hr at 37° C. Trypsin was added to a final 1:50 (w/w) enzyme-to-protein ratio for overnight digestion. The digested peptides were acidified with trifluoroacetic acid (TFA) to final concentration of 0.5% TFA, and 250 ul of Ethyl acetate was added to 250 ul digested solution. The mixture was shaken for 2 min, then centrifuged at 13,200 rpm for 2 min to obtain aqueous and organic phases. The aqueous phase was collected and desalted using a 100 mg of Sep-pak C18 column (Waters, Milford, Mass.).

Phosphopeptide Enrichment

The phosphopeptide enrichment was performed according to the reported protocol with some modifications. The in-house-constructed IMAC tip was made by capping the end with a 20 μm polypropylene frits disk (Agilent, Wilmington, Del., USA). The tip was packed with 5 mg of Ni-NTA silica resin by centrifugation. Prior to sample loading, $Ni^{2+}$ ions were removed by 100 mM EDTA solution. Furthermore, the beads were chelating with $Fe^{3+}$ and equilibrated with loading buffer (6% (v/v) acetic acid (AA) at pH 2.7). Tryptic peptides were reconstituted in loading buffer and loaded onto the IMAC tip. After successive washes with 4% (v/v) AA, 25% ACN, and 6% (v/v) AA, the bound phosphopeptides were eluted with 200 mM $NH_4H_2PO_4$. The eluted phosphopeptides were desalted using C-18 StageTips.

LC-MS/MS Analysis

Phosphopeptides were dissolved in 4 μL of 0.3% formic acid (FA) with 3% ACN and injected into an Easy-nLC 1000 (Thermo Fisher Scientific). Peptides were separated on a 45 cm in-house packed column (360 μm OD×75 μm ID) containing C18 resin (2.2 μm, 100 Å, Michrom Bioresources) with a 30 cm column heater (Analytical Sales and Services) and the temperature was set at 50° C. The mobile phase buffer consisted of 0.1% FA in ultra-pure water (buffer A) with an eluting buffer of 0.1% FA in 80% ACN (buffer B) ran with a linear 45 min or 60 min gradient of 6%-30% buffer B at flow rate of 250 nL/min. The Easy-nLC 1000 was coupled online with a hybrid high resolution LTQ-Orbitrap Velos Pro mass spectrometer (Thermo Fisher Scientific). The mass spectrometer was operated in the data-dependent mode in which a full-scan MS (from m/z 350-1500 with the resolution of 30,000 at m/z 400) followed by MS/MS on the 10 most intense ions (normalized collision energy (NCE) 30%, AGC 3E4, max injection time 100 ms).

Data Processing

The raw files were searched directly against UniprotKB database version January 2015 with no redundant entries using MaxQuant software (version 1.5.4.1) with Andromeda search engine. Initial precursor mass tolerance was set at 20 ppm and the final tolerance was set at 6 ppm, and ITMS MS/MS tolerance was set at 0.6 Da. Search criteria included a static carbamidomethylation of cysteines (+57.0214 Da) and variable modifications of (1) oxidation (+15.9949 Da) on methionine residues, (2) acetylation (+42.011 Da) at N-terminus of protein, and (3) phosphorylation (+79.996 Da) on serine, threonine or tyrosine residues were searched. Search was performed with Trypsin/P digestion and allowed a maximum of two missed cleavages on the peptides analyzed from the sequence database. The false discovery rates of proteins, peptides and phosphosites were set at 0.01. The minimum peptide length was six amino acids, and a minimum Andromeda score was set at 40 for modified peptides. A site localization probability of 0.75 was used as the cut-off for localization of phosphorylation sites. All the peptide spectral matches and MS/MS spectra can be viewed through MaxQuant viewer. All the localized phosphorylation sites and corresponding phosphoproteins were submitted to pLogo software and Panther to determine the phosphorylation motifs and gene ontology, respectively.

Parallel Reaction Monitoring (PRM)

Peptide samples were dissolved in 8 μl of 0.1% formic acid and injected 6 ul into easy-nLC 1200 (Thermo Fisher) HPLC system. Eluent was introduced into the mass spectrometer using 10 cm PicoChip® columns filled with 3 uM Reprosil-PUR C18 (New Objective, Woburn, Mass.) operated at 2.6 kV. The mobile phase buffer consists of 0.1% formic acid in water with an eluting buffer of 0.1% formic acid (Buffer A) in 90% CH3CN (Buffer B). The LC flow rate was 300 nl/min. The gradient was set as 0-30% Buffer B for 30 mins and 30-80% for 10 mins. The sample was acquired on QExactive HF (Thermo Fisher). Each sample was analyzed under parallel reaction monitoring (PRM) with an isolation width of ±0.7 Th. In all experiments, a full mass spectrum at 60,000 resolution relative to m/z 200 (AGC target 3E6, 100 ms maximum injection time, m/z 400-1600) was followed by up to 20 PRM scans at 15000 resolution (AGC target 1E5, 50 ms maximum injection time) as triggered by a unscheduled inclusion list. Higher-energy collisional dissociation (HCD) was used with 30 eV normalized collision energy. PRM data were manually curated within Skyline (version 3.5.0.9319)

Quantitative Data Analysis

All data were analyzed using the Perseus software (version 1.5.4.1). For the quantification of both proteomic and phosphoproteomic data, the intensities of peptides and phosphopeptides were extracted by MaxQuant, and the missing values of intensities were replaced by normal distribution with a downshift of 1.8 standard deviations and a width of 0.3 standard deviations. The significantly increased phosphosites or proteins in patient samples were identified by the p-value which is significant based on a two sample t-test with a permutation-based FDR cut-off 0.05 with S0 set on 0.2 for all of data sets. The up-regulated candidate networks were predicted in STRING version 10.0 with the interaction score ≥0.4, and the signal networks were visualized using Cytoscape version 3.4.0 with MCODE plugin version 1.4.2. All the mass spectrometric data have been deposited to the PRIDE partner repository with the dataset identifier PXD005214.
(http://www.ebi.ac.uk/pride; username: reviewer96194@ebi.ac.uk; password: Pzv4cB0v).

EXAMPLES

Example 1

Identification of 9,643 Unique Phosphopeptides From Plasma Microvesicles and Exosomes In this Example, we illustrated the preliminary screening of phosphopeptides from plasma microvesicles and exosomes.

The workflow for the isolation of EVs, enrichment of phosphopeptides, and EV phosphoproteome analyses is illustrated in FIG. 1. Microvesicles and exosomes were isolated from human plasma samples through high-speed and ultra-high-speed centrifugations, respectively, an approach that has been employed in multiple studies and can effectively isolate EVs in good purity. For initial screening, the plasma samples were collected and pooled from healthy individuals (n=6) and from patients diagnosed with breast cancer (n=18). After lysis of EVs, proteins were extracted and peptides were generated using trypsin with the aid of phase-transfer surfactants (PTS) for better digestion efficiency and fewer missed tryptic sites. Phosphopeptides were enriched and followed by LC-MS/MS analyses. For each phosphopeptide sample, three technical replicates were performed. Label-free quantification was performed to determine differential phosphorylation of EV proteins in control from those in patient plasma samples.

Figure 2:
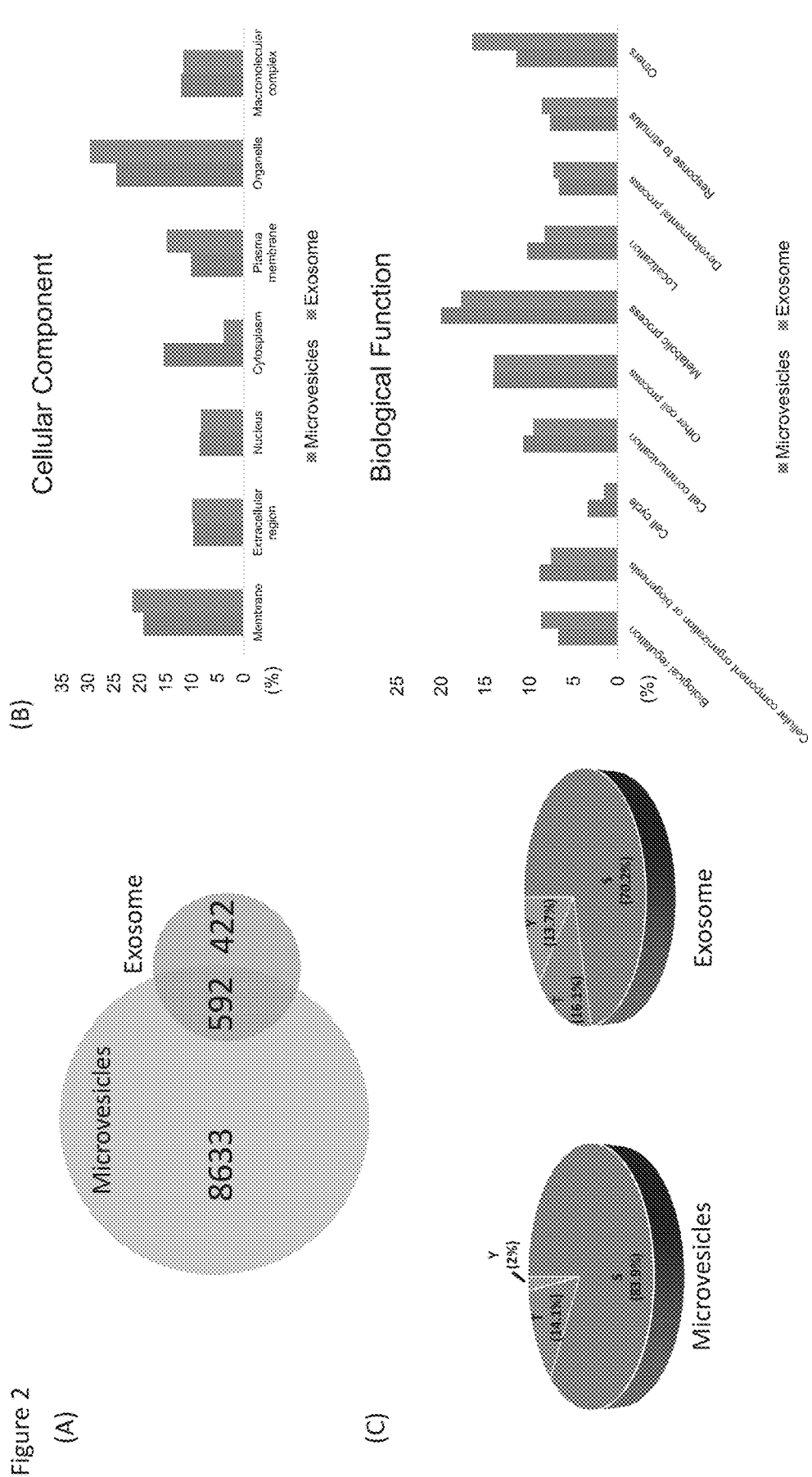
FIG. 2 (A) The Venn diagram shown the number of identified phosphopeptides and overlap between microvesicles and exosomes. (B) Classification of the identified phosphoproteins based on cellular component and biological function. (C) The distribution of S/T/Y phosphopeptides in microvesicles and exosomes.

The strategy allowed us to identify 9643 unique phosphopeptides, including 9,225 from microvesicles and 1,014 from exosomes, representing 1,934 and 479 phosphoproteins in microvesicles and exosomes, respectively. On average, close to 7000 unique EV phosphopeptides were identified from 1 ml of human plasma. More than 50% of exosome phosphopeptides were also identified in microvesicles (FIG. 2A). Gene ontological (GO) analysis of phosphoproteins found in microvesicles or exosomes indicated overall similar cellular components and biological function (FIG. 2B). While previously large scale phosphoproteomics studies revealed that phosphorylation preferentially targets nuclear proteins, a significant portion of the EV phosphoproteomes are distinctively from membrane and organelles. As expected, proteins annotated as extracellular were significantly overrepresented in the EV phosphoproteomes. We also found that many EV phosphoproteins are involved in cell-cell communication, stimulus response, and biogenesis.

Figure 6:
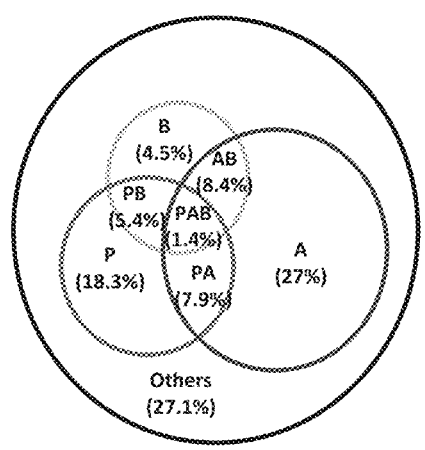
FIG. 6 (A) Classification of phosphosites based on kinase specificities (P, proline-directed; A, acidiphilic; B, basophilic; Others); (B) The summary of motifs were extracted from the sequence windows of identified probability >0.75 phosphorylation sites by pLogo.
Figure 6:
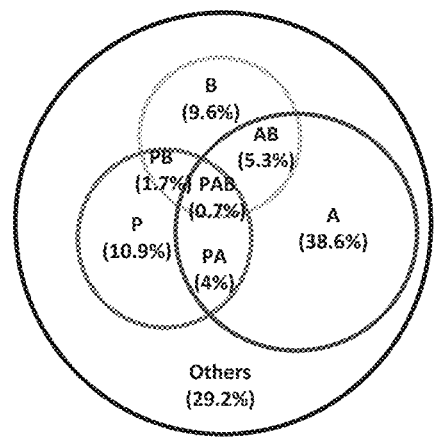
Figure 6:
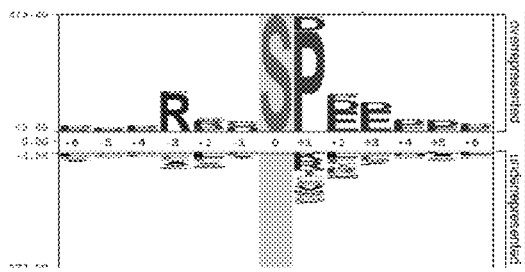
Figure 6:
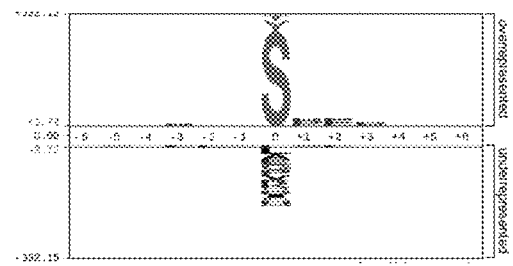

The EV phosphoproteome analyses suggested that the distribution of pY, pT and pS sites is 2.0%, 14.1% and 83.9%, respectively, for microvesicle phosphoproteins, which is similar to previously reported site distribution in in vivo human phosphoproteomes. Interestingly, the distribution of pY in exosomes is an order of magnitude higher, 13.7%, quite close to the distribution of pT, 16.1% (FIG. 2C). This apparent discrepancy may reflect the different origins of microvesicles and exosomes. Microvesicles bud directly from the plasma membrane while exosomes are represented by endosome-associated proteins, in which proteins such as integrins, hormone receptors, growth factor receptors, receptor tyrosine kinases, and non-receptor tyrosine kinases such as Src kinases are involved. A further motif analysis of pS/T phosphorylation sites revealed overall similar distribution of general motif to cellular phosphoproteome, e.g., the most abundant class of sites is acidophilic, followed by proline-directed and basophilic (FIG. 6). However, in exosome phosphoproteome, proline-directed phosphorylation constitutes only half of that in microvesicles.

Example 2

Cancer Specific Phosphoproteins in EV

In this Example, we establish that looking the differences of EV phosphoprotein level from patient sample and healthy donor sample may identify a panel of phosphoproteins as the biomarker for diagnosing the disease at issue.

Figure 3:
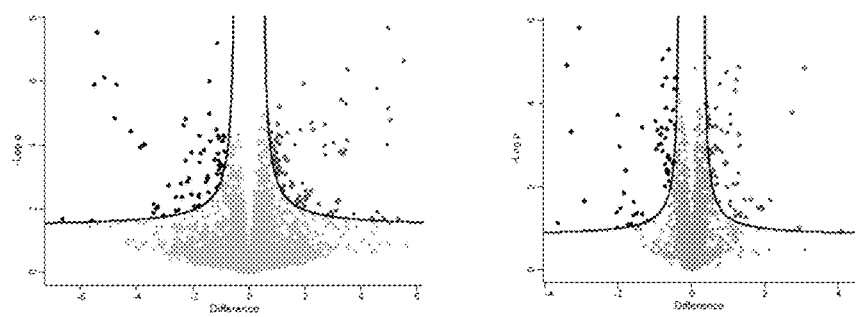
FIG. 3 (A) The volcano plots represent the phosphoproteome (left) and proteome (right) comparisons of microvesicles and exosomes in breast cancer patients versus healthy controls. Significant changes in proteins and phosphosites in breast cancer that were identified through a permutation-based FDR t-test (FDR=0.05, and S0=0.2). The significant up-regulated proteins and sites are colored in red, and down-regulated are colored in black. (B) The number of identified phosphopeptides (class 1), quantified phosphosites (class 2), and significantly changed phosphosites (class 3) in label free quantification. See supplementary tables for more detailed information. (C) The Venn diagram shown the protein overlap between phosphoproteome and proteome in microvesicles and exosome.
Figure 3:
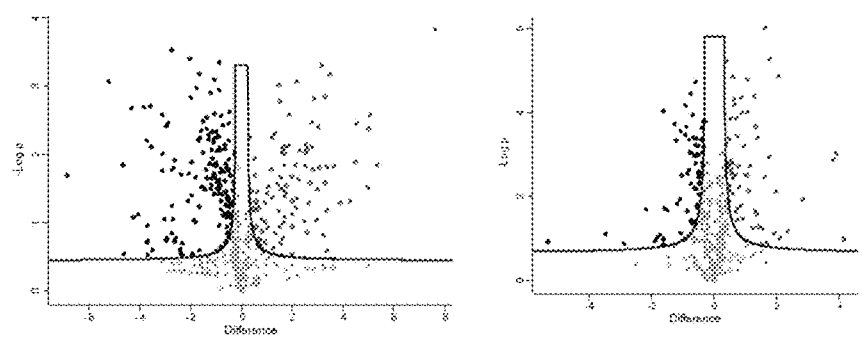
Figure 3:
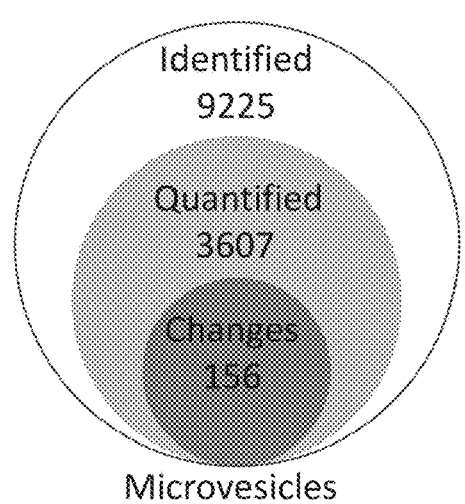
Figure 3:
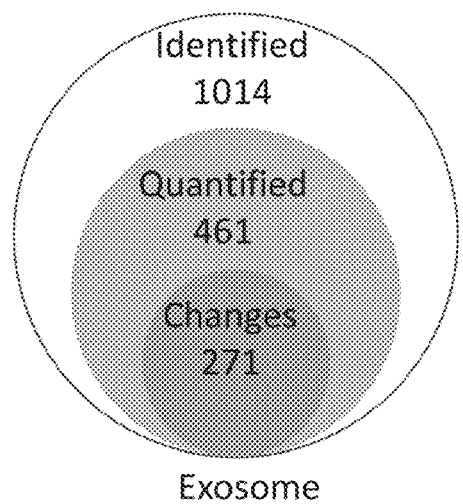
Figure 3:
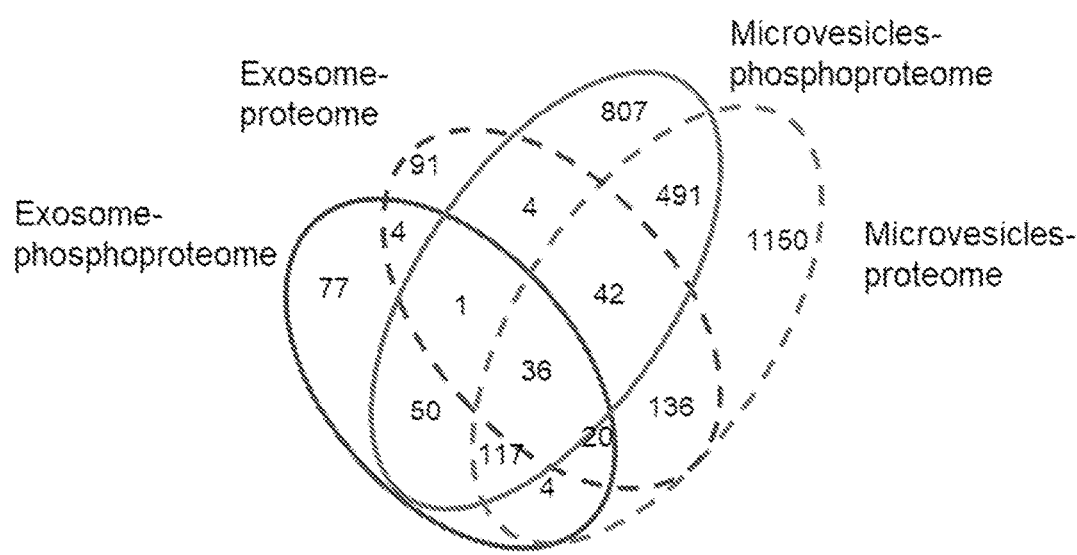

Label-free quantitation of phosphopeptides with probability score of phosphorylation site location over 0.75 was used to identify differential phosphorylation events in breast cancer patients from healthy individuals. We quantified 3,607 and 461 unique phosphopeptides and identified 156 and 271 phosphopeptides with significant changes (FDR<0.05 and S0=0.2) in microvesicles and exosomes, respectively (FIGS. 3A&B). Differential phosphorylation may be a result of changes in protein expression or changes in a particular site's phosphorylation. To distinguish these factors, we also performed the label-free quantitation of total proteomes for both microvesicles and exosomes (FIG. 3C). Altogether, we identified 1,996 proteins, 34.4% of which were also identified with phosphopeptide enrichment. By comparison, 862 proteins were detected in the phosphorylation data alone, indicating that phosphoproteins are typically of low abundance, escaping detection via the shotgun proteomic approach. Quantitative analyses of EV proteomes revealed strikingly similar expression of most proteins in healthy individuals and cancer patients (FIG. 3A). In comparison, we identified a larger number of phosphorylation sites with significantly higher change in patient samples, indicating that these phosphorylation differences between cancer patients and healthy individuals are not due to changes in protein expression, and thus reflect true differential cancer patient-specific phosphorylation. The result also justifies our approach to develop protein phosphorylation changes, instead of protein expression changes, as the measurement of disease progression.

We compared 197 unique phosphopeptides that showed significant increase in cancer patients with a recent comprehensive proteogenomic study in which breast phosphoproteomics studies were carried out in tissues from 105 breast cancer patients. A significant portion of these 197 phosphopeptides (>60%) were also identified by the study (FIG. 4A), indicating that EV phosphoproteome is sensitive and quantitative analyses of EV phosphoproteomics can identify phosphorylation events that are disease specific. The results also highlight the advantage of analyzing EV phosphoproteome through liquid biopsy over tissue biopsy which is invasive and subject to variation due to long procedure.

Figure 4:
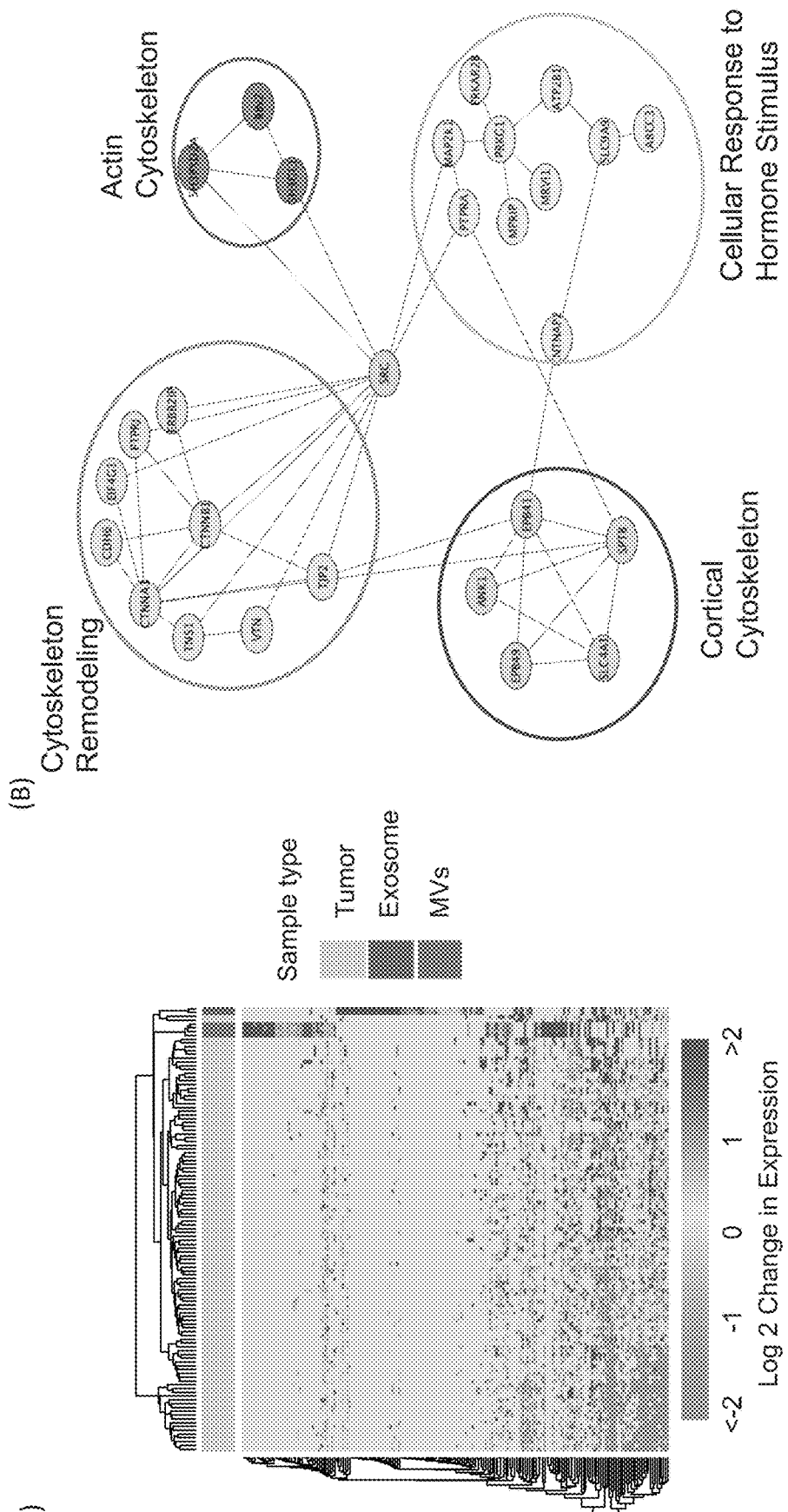
FIG. 4 (A) The hierarchical clustering analysis of up-regulated phosphopeptides conveys the overlap between EVs in this study and breast cancer tissues by Mertins et. al. The top bars shown the clustering of different samples, Grey represent the tumor samples analyzed in Mertins et. al., while blue bars are replicates of MV analysis and cobalt green are exosome analysis in this study. The fold change is shown in log 2 value; (B) The STRING network analysis of up-regulated phosphoproteins in EVs.

To better understand the biological roles of differential phosphorylation events, we examined cancer patient-specific phosphoproteins using STRING to identify enriched GO categories and signaling network. We found that several crucial functions related to cancer metastasis, membrane re-organization, and intercellular communication were enriched in cancer specific EV phosphoproteins (FIG. 4B).

Example 3

Verification of Cancer Patient-Specific Phosphorylation Using PRM

In this Example we further validated the phosphoprotein biomarker candidate identified in Example 2.

Since breast cancer is extremely heterogeneous, the chance to identify a single diagnostic biomarker is likely rare. Instead, the identification of a panel of candidate markers that reflect the onset and progression of key disease-related signaling events would be feasible to offer better prognostic value. In effort to validate the differential phosphorylation of potential markers in cancer patients, we applied Parallel Reaction Monitoring (PRM) to quantify individual EV phosphopeptides in plasma from breast cancer patients and healthy individuals. Since phospho-specific antibodies suitable for construction of enzyme-linked immunosorbent assay (ELISA) are rarely available, targeted, quantitative MS approaches such as PRM and MRM (multi-reaction monitoring) are essential for initial validation. As a demonstration that PRM can be used to initially verify candidate phosphoproteins, we selected four phosphoproteins, Ral GTPase-activating protein subunit alpha-2 (RAL-GAPA2), cGMP-dependent protein kinase1 (PKG1), tight junction protein 2 (TJP2), and nuclear transcription factor, X box-binding protein 1 (NFX1), that showed significant phosphorylation up-regulation in cancer patients for PRM. In addition, these four proteins were previously reported as phosphoproteins and implicated in multiple breast cancer study.

Figure 5:
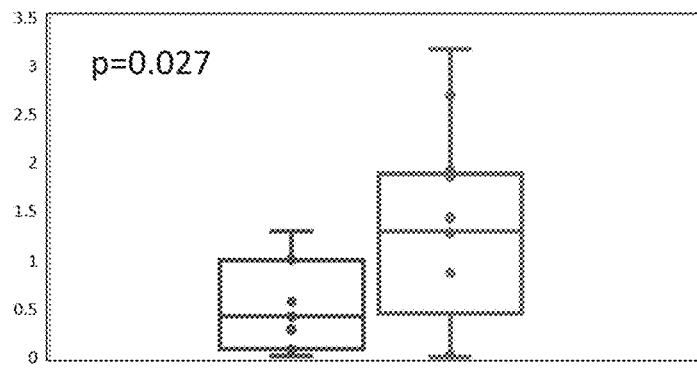
FIG. 5 Four potential markers were validated in 13 breast cancer patients and 6 healthy individuals using PRM. Three potential markers, RALGAPA2, PRKG1, and TJP2, show significant difference ($p<0.05$) in breast cancer patients compared to healthy controls.
Figure 5:
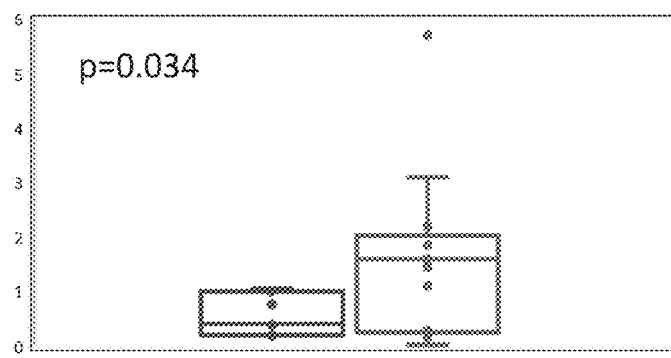
Figure 5:
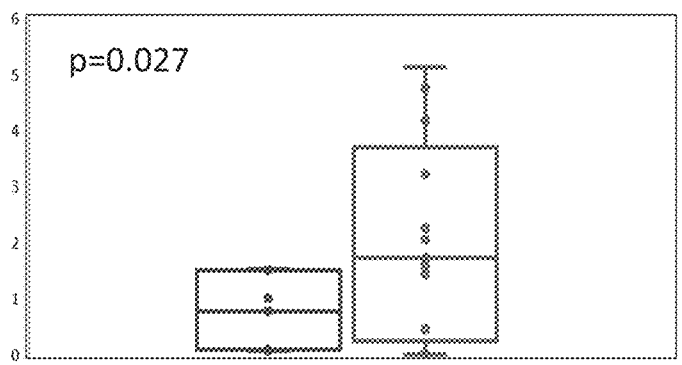
Figure 5:
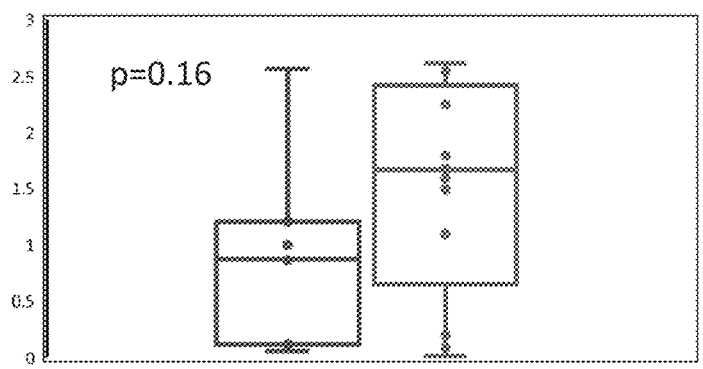

Quantitative assays based on PRM were performed with plasma EV samples from 13 cancer patients and 7 healthy controls. The relative abundance data of phosphopeptides from four individual proteins are presented as a linear box-and-whiskers plot (FIG. 5). With reference from the figure, RALGAPA2, PKG 1 and TJP2 were observed to be significantly elevated in breast cancer patients than in controls. However, the fold difference is noticeably smaller in PRM than label-free quantification. In particular, NFX1 phosphorylation was only identified in breast cancer samples and not in healthy controls, but due to large variation among individual samples, the difference of NFX1 phosphorylation on the specific site is statistically inconclusive. The data may be the reflection of dynamic suppression of targeted proteomics such as MRM and PRM. Nevertheless, large variation among clinical samples underscores current challenges facing biomarker validation.

The invention claimed is:

1. A method for preparing phosphoproteins from a patient, comprising:
   (i) Selectively isolating extracellular vesicles (EVs) in an aliquot of plasma from a blood sample of a patient;
   (ii) Enriching phosphoproteins in said isolated EVs; and
   (iii) quantifying at least Ral GTPase-activating protein subunit alpha-2 (RAL-GAPA2), cGMP-dependent protein kinase 1 (PKG1), and tight junction protein 2 (TJP2) levels in said enriched phosphoproteins.

2. The method according to claim 1, further comprising identifying the presence of one or more glycoproteins from the patient EVs-using non-antibody based quantitation.

3. A method of identifying the presence or absence of signature proteins in a subject comprising:
   obtaining or having obtained a plasma sample from a subject;
   selectively isolating a population of extracellular vesicles (EVs) in the sample;
   identifying the presence of signature proteins in the population of EVs using non-antibody based quantitation; and
   quantifying a level of expression of the identified signature proteins in the population of EVs using parallel reaction monitoring (PRM) or multi-reaction monitoring (MRM);
   wherein the signature proteins comprise at least Ral GTPase -activating protein subunit alpha-2 (RAL-GAPA2), cGMP-dependent protein kinase 1 (PKG1), and tight junction protein 2 (TJP2).

4. The method of claim 1, wherein the EVs comprise microvesicles and exosomes.

5. The method of claim 3, wherein the non-antibody based quantitation comprises mass spectrometry.

6. The method of claim 3, wherein the signature proteins further comprise nuclear transcription factor X box-binding protein 1 (NFX1).

7. The method of claim 3, wherein the EVs comprise microvesicles and exosomes.

8. The method of claim 1, wherein the step of quantifying at least RAL-GAPA2, PKG1, and TJP2 levels comprises using quantitative mass spectrometry.

9. The method of claim 8, wherein the quantitative mass spectrometry comprises parallel reaction monitoring (PRM) or multi-reaction monitoring (MRM).

10. The method of claim 8, wherein the quantitative mass spectrometry is performed in tandem with liquid chromatography (LC-MS/MS).

11. The method of claim 1, wherein:
    selectively isolating EVs comprises using sequential high-speed centrifugation;
    enriching phosphoproteins in said isolated EVs is performed using immobilized metal affinity chromatography (IMAC); and
    quantifying at least RAL-GAPA2, PKG1, and TJP2 levels comprises using label-free quantitative phosphoproteomics.

12. The method of claim 11 wherein the sequential high-speed centrifugation comprises at least a first series of centrifugation at at least 20,000×g and a second series of centrifugation at at least 100,000×g.

13. The method of claim 12, wherein the first series of centrifugation comprises at least two rounds of centrifugation at at least 20,000×g and the second series of centrifugation comprises at least two rounds of centrifugation at at least 100,000×g.

* * * * *